(12) United States Patent
Gibson et al.

(10) Patent No.: US 6,534,488 B1
(45) Date of Patent: Mar. 18, 2003

(54) RADIOLABELLED BISPHOSPHONATES AND METHOD

(75) Inventors: Alexander Mark Gibson, Amersham (GB); Marivi Mendizabal, Amersham (GB); Richard Pither, Amersham (GB); Shirley Elizabeth Pullan, Amersham (GB); Vaughan Griffiths, London (GB); Philip Duncanson, London (GB)

(73) Assignee: Amersham plc, Amersham (GB)

( * ) Notice: Subject to any disclaimer, the term of this patent is extended or adjusted under 35 U.S.C. 154(b) by 0 days.

(21) Appl. No.: 10/031,760

(22) PCT Filed: Aug. 2, 2000

(86) PCT No.: PCT/EP00/07490

§ 371 (c)(1),
(2), (4) Date: May 8, 2002

(87) PCT Pub. No.: WO01/09146

PCT Pub. Date: Feb. 8, 2001

(30) Foreign Application Priority Data

Aug. 3, 1999 (EP) .............................. 99306189

(51) Int. Cl.⁷ .............................. C07F 9/38; C07F 9/44; A61K 31/663
(52) U.S. Cl. ........................................ 514/102; 562/13
(58) Field of Search ............................. 562/13; 514/102

(56) References Cited

U.S. PATENT DOCUMENTS 3,965,254 A 6/1976 Tofe

FOREIGN PATENT DOCUMENTS

DE 197 37 460 A 3/1999
WO WO 92 11267 A 7/1992

OTHER PUBLICATIONS

R.M. Schoth, et al. "Routes to F3–etidronic acid (1–hydroxy–2,2,2–trifluoroethylidene–bisphosphonic acid), molecular structure of the tris(trimethylsilyl)ester, antimineralization, and antiresorption effects of the disodium salt" Naturwissenschaften 1996, vol. 83 (12), pp. 571–574.

*Primary Examiner*—Taofiq Solola
(74) *Attorney, Agent, or Firm*—Royal N. Ronning, Jr.; Stephen G. Ryan

(57) ABSTRACT

The present invention relates to $^{32}$P or $^{33}$P-labelled bisphosphonates as radiotherapeutic radiopharmaceuticals. The $^{32}$P- or $^{33}$P-labelled bisphosphonates, which are chemically identical to the unlabelled agent, are expected to target the lesion site in an identical manner, but also deliver a significant radiocytotoxic effect to the surrounding cells. This should result, given the favorable energetics of the β particle emission from the $^{33}$P nuclide, in a loss of proliferative capacity of cells associated with the tumor lesion. The relative stability and in vivo localisation of bisphosphonates makes them good candidates as $^{32}$P/$^{33}$P delivery vehicles.

14 Claims, No Drawings

RADIOLABELLED BISPHOSPHONATES AND METHOD

This application is a 371 of PCT/EP00/07490 filed Aug. 2, 2000.

FIELD OF THE INVENTION

The present invention relates to $^{32}$P- or $^{33}$P-labelled bisphosphonates as radiotherapeutic radiopharmaceuticals. The $^{32}$P or $^{33}$P-labelled bisphosphonates, which are chemically identical to the unlabelled agent, are expected to target the lesion site in an identical manner, but also deliver a significant radiocytotoxic effect to the surrounding cells. This should result, given the favourable energetics of the β particle emission from the $^{32}$P nuclide, in a loss of proliferative capacity of cells associated with the tumour lesion. The relative stability and in vivo localisation of bisphosphonates makes them good candidates as $^{32}$P/$^{33}$P delivery vehicles.

BACKGROUND OF THE INVENTION

Bisphosphonates are known as palliatives to treat osteosarcoma or bone metastases associated with carcinoma such as breast or prostate. These agents, such as Pamidronate and Clodronate, exert a negative effect upon osteoclasts at the site of the lesion resulting in decreased bone resorption at this site. Bisphosphonates, however, appear to lose activity with time necessitating repeat administration.

There have been extensive examples of bisphosphonate syntheses in the literature over the last 25 years. Synthesis of the α-hydroxyl-methylene bisphosphonates, those most commonly studied with respect to bone disorders, have largely been performed under harsh conditions of elevated temperatures, often resulting in low-yielding reactions. The common route of synthesis to such compounds involves heating a source of phosphorus, usually phosphorous acid, with the appropriate carboxylic acid and $PCl_3$. This synthesis is not ideal for the incorporation of $^{32/33}$P into a bisphosphonate, due to the safety and radiological hazards associated with volatile $^{32/33}PCl_3$, and the fact that the primary role of the $PCl_3$ is to generate an activated carbonyl compound rather than as a source of the phosphonate groups. The poor yields often obtained from the traditional syntheses are not appropriate for radiolabelling with an expensive radionuclide.

Tris(trimethylsilyl) phosphite, $P(OTms)_3$, has been isynthesised from $PCl_3$ and, alternatively, from phosphorous acid and, subsequently, used to introduce phosphorus into compounds.

U.S. Pat. No. 3,965,254 describes the use of $^{32/33}$P in bisphosphonates for the treatment of bone cancer. It was shown that the $^{32}$P or $^{33}$P radionuclide could be targeted to the tumour site. The patent describes the incorporation of $^{32}$P into EHDP (disodium ethane-1-hydroxy-1,1-diphosphonate) and its subsequent use in in vivo studies. The synthesis used to generate the radiolabelled bisphosphonates followed the conventional synthesis using $^{32/33}PCl_3$. Within the synthetic route the reaction is, at times heated to 145° C. for up to 6 hours and a reflux of 40 hours duration. The final yield was approximately 65%. This route of preparation for these compounds is seen as inappropriate for the reasons outlined above.

Accordingly, it is one object of this invention to supply a convenient and improved route of synthesis for radiolabelled bisphosphonates, for the use in therapeutic treatment of bone metastatic disease.

SUMMARY OF THE INVENTION

In one aspect the invention provides a method of making a bisphosphonate, which method comprises reacting a tris (silyl)phosphite with an activated carbonyl compound and hydrolysing the resulting intermediate according to the reaction scheme:

where
  each X is the same or different and is tri-($C_1$–$C_{12}$ hydrocarbyl)silyl,
  R is $C_1$–$C_{12}$ alkyl, $C_2$–$C_{12}$ alkenyl, $C_2$–$C_{12}$ alkynyl, $C_2$–$C_{12}$ aryl (including heteroaryl) or substituted variants of these where functionalised groups, if present, are appropriately masked (ie. protected) during the synthesis,
  and Y is an activating moiety.

The functional group(s) of the 'substituted variants' can be amino (primary, secondary or tertiary), hydroxy, alkoxy or fluorine. R is preferably $C_1$–$C_{12}$ alkyl, $C_1$–$C_{12}$ fluoroalkyl or $C_1$–$C_{12}$ primary, secondary or tertiary aminoalkyl or a derivative of these, or a substituted alkyl group containing nitrogen as part of a heterocyclic ring system. R is most preferably $C_1$–$C_6$ alkyl or $C_2$–$C_9$ primary, secondary or tertiary aminoalkyl. Preferred $C_2$–$C_9$ aminoalkyl groups are —$(CH_2)_pNQ_2$ where p is 2 or 3 and Q is H or $C_1$–$C_5$ alkyl, with —$(CH_2)_2NH_2$, —$(CH_2)_3NH_2$ and $(CH_2)_3NMe$(pentyl) being especially preferred.

In the starting tris(silyl)phosphite $P(OX)_3$, X is tri-($C_1$–$C_{12}$ hydrocarbyl)silyl, e.g. trialkylsilyl or triarylsilyl, conveniently trimethylsilyl since derivatised trimethylsilanes are readily commercially available. Mixed phosphites are possible and may be preferred.

The starting activated carbonyl compound of formula RCO.Y is preferably an acid halide, particularly an acid chloride or acid bromide; an acid anhydride; an α-ketophosphonate; or an active ester such as that derived from N-hydroxysuccinimide. Hence the activating moiety Y can be: a leaving group such as halogen (especially Cl or Br), or an acid anhydride linkage $(RCO)_2O$, or an active ester, examples of which are well known to those skilled in the art. Alternatively, Y can be a phosphonate —$PO(OR''')_2$, ie. RCOY may be an α-ketophosphonate. Preparation of bisphosphonates has also been achieved using an active ester derived from 2-hydroxypyridine and also acid anhydrides. Active esters derived from pentafluorophenol and hydroxybenztriazole are also possible. These reactions show how the increased nucleophilicity of the silylated phosphites (compared with trialkyl phosphites) permits the use of much less activated carbonyl compounds in the formation of the desired products.

When Y is a leaving group, the Intermediate generally has the formula $RC(OZ)(PO.[OX]_2)_2$ where Z is H or X. When RCOY is an α-ketophosphonate, an addition reaction rather than a substitution reaction may take place, e.g.:

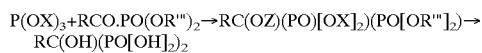

where R''' is $C_{1-12}$ alkyl or X (by treatment of the —O-alkyl system with TmsBr or Tmsl).

The R group is chosen to provide a desired substituent on the hydroxymethane-bisphosphonate unit.

Various bisphosphonate drugs $R^1CR^2(PO[OH]_2)_2$ have been commercialised as follows:

| Name | R¹ | R² |
|---|---|---|
| Etidronate | OH | —$CH_3$ |
| Ibandronate | OH | —$CH_2CH_2$NMe(pentyl) |
| Alendronate | OH | —$(CH_2)_3NH_2$ |
| Pamidronate | OH | —$(CH_2)_2NH_2$ |
| Clodronate | Cl | Cl |

Preferably the tris(silyl)phosphite contains $^{32}P$ or $^{33}P$, either at 100% abundance or at least at an artificially high isotopic abundance of e.g. at least 1%. Preferably 2 molar equivalents of the tris(silyl)phosphite are reacted with 1 molar equivalent of the activated carbonyl compound. Although use of elevated temperatures is possible, the reaction is found to go in high yield at ambient temperature, thus providing a convenient route for introducing $^{32}P$ or $^{33}P$ into a bisphosphonate molecule of choice.

Dry aprotic solvents such as diethyl ether or tetrahydrofuran can be used to help facilitate handling of the reactants. Reaction times depend on the leaving group and on the quantity of solvent used. With modest quantities of solvent, reaction times are typically 10 to 15 min with an acid chloride or anhydride but it can require heating for several hours with less activated carbonyl compounds.

There results an intermediate having the formula $RC(OZ)(PO.[OX]_2)_2$ or $RC(OZ)(PO)[OX]_2)(PO[OR'''])$. In general these intermediates are believed novel and form further aspects of this invention. They may readily be hydrolysed to the desired bisphosphonates by the addition of excess methanol or water at elevated or preferably ambient temperature. Some of the resulting bisphosphonates are new compounds.

Thus the invention also provides radiolabelled bisphosphonates of the formula:

$$R''C(OH)(^nPO[OH]_2)_2$$

where n is at least partly 32 or 33 whereby the compound contains an artificially high proportion of $^{32}P$ or $^{33}P$, and R" is $C_1-C_{12}$ primary, secondary or tertiary aminoalkyl or a derivative of these, or a substituted alkyl group containing nitrogen as part of a heterocyclic ring system. R" is preferably $C_2-C_9$ primary, secondary or tertiary aminoalkyl, most preferably —$(CH_2)_pNQ_2$ where p is 2 or 3 and Q is H or $C_1-C_5$ alkyl, with —$(CH_2)_2NH_2$, —$(CH_2)_3NH_2$ and $(CH_2)_3$NMe(pentyl) being especially preferred.

It may be advantageous to provide one of the starting reagents, e.g. the tris(silyl)phosphite $POX_3$ or the activated carbonyl compound RCOY, in immobilised form. This facilitates purification of the starting compound, which may be particularly useful when an isotopically labelled phosphite is used, and also facilitates purification of the desired bisphosphonate product.

The radiolabelled bisphosphonates of the present invention have useful properties as palliatives to treat osteosarcoma or bone metastasis associated with carcinoma such as breast or prostate, with the additional advantage of comprising an artificially high isotopic abundance of $^{32}P$ or $^{33}P$ for targeting either bone metastasis or tumours or other diseases so that may be treated with radiotherapy.

Also included within the scope of the invention are radiolabelled phosphorus compounds of the formula $$R'_q{}^nP(OX)_{3-q}$$

where

R' is $C_1-C_{12}$ alkyl or $C_2-C_{12}$ aryl, q is 0, 1 or 2, n is at least partly 32 or 33 whereby the compound contains an artificially high proportion of $^{32}P$ or $^{33}P$, each X is the same or different and is tri-($C_1-C_{12}$ hydrocarbyl)silyl.

When q is 0, these are radiolabelled trialkylsilylphosphites, useful as starting materials in the method of the invention described above.

DETAILED DESCRIPTION OF INVENTION

EXAMPLE 1

Preparation of Tris(trimethylsilyl) Phosphite (compound 1)

Triethylamine (40.4 g, 40.4 mmol) was added dropwise to a mechanically stirred solution of phosphorous acid (16.5 g, 201 mmol) and chlorotrimethylsilane (44 g, 405 mmol) in diethyl ether (1200 cm³). Immediately, a white precipitate of triethylamine hydrochloride formed. After the addition was complete (2 h) the mixture was stirred for a further 2 hours. The insoluble salt was removed by filtration and the filtrate concentrated to about 200 cm³. The small quantity of additional precipitate formed during this process was subsequently filtered off and the filtrate evaporated to give a cloudy liquid. The product was purified by distillation under reduced pressure, the fraction boiling in the range 45–50° C. at 0.1 mbar being collected. The bis(trimethylsilyl) phosphite was isolated as a colourless oil (35 g, 77%). $^{31}P$ NMR: δ–12.8. Chlorotrimethylsilane (20 g, 185 mmol) was added dropwise to a stirred solution of bis(trimethylsilyl)phosphite (30 g, 132 mmol) and N,N-diethyltrimethylsilylamine (20 g, 137 mmol) and the mixture stirred at room temperature for 1 h. The solid formed was removed by filtration and the filtrate distilled in vacuo. A colourless fraction boiling at 77–80° C. at 0.1 mbar was collected (30 g, 75%). $^{31}P$ NMR: δ+116.3.

EXAMPLE 2

Synthesis of Hydroxyethylidene Bisphosphonic Acid (compound 2)

Tris(trimethylsilyl) phosphite (2 molar equiv.) in an appropriate dry solvent was added dropwise to a stirred solution of acetyl chloride (1 molar equiv.) in an appropriate dry solvent at room temperature and the mixture stirred for 10 minutes. Excess methanol was then added and the mixture stirred for 5 minutes to decompose the silyl esters. The volatile components in the reaction mixture were then removed under reduced pressure to leave the title compound in good purity.

It is anticipated that this reaction can be performed using $^{32}P(OTms)_3$ or $^{33}P(OTms)_3$ in order to introduce a $^{32}P$ label or a $^{33}P$ label.

Compounds 2 and 3

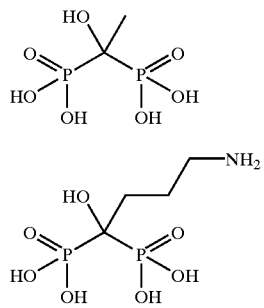

EXAMPLE 3

Synthesis of 4-Amino-1-hydroxybutane-1,1-bisphosphonic Acid (compound 3)

A solution of benzylchloroformate (9.4 g, 5.5 mmol) in acetone (15 ml) was added dropwise to a mixture of 4-aminobutanoic acid (5.2 g, 5 mmol), sodium bicarbonate (8.6 g, 10 mmol), water (25 ml) and acetone (25 ml) causing vigorous effervescence. The solution was allowed to stir overnight. The acetone was removed using a rotary evaporator to leave an aqueous phase which was washed with ether (2×25 ml). The resulting aqueous layer was acidified to pH2 with dilute hydrochloric acid and then extracted with dichloromethane (3×50 ml). The dichloromethane extracts were combined, dried over magnesium sulphate and volatile components removed under reduced pressure to leave 4-[(benzyloxycarbonyl)amino]butanoic acid as a white solid in a good state of purity. This material was used without further purification.

A solution of dicyclohexylcarbodiimide (2.5 g, 12 mmol) in dry tetrahydrofuran (10 ml) was added in one portion to a stirred solution of 4-[(benzyloxycarbonyl)amino] butanoic acid (2.4 g, 10 mmol) and N-hydroxysuccinimide (1.5 g, 13 mmol) in dry tetrahydrofuran (10 ml). After about 20 minutes dicyclohexylurea began to precipitate from the solution. Stirring was continued for 16 hours and the resulting solution was then filtered. The insoluble white solid was removed and washed with tetrahydrofuran (20 ml) and the washings combined with the filtrate. Volatile components were removed from the tetrahydrofuran solution in vacuo to leave a white waxy solid. This residue was purified by chromatography on silica using ethyl acetate as the eluant. Removal of the solvent under reduced pressure gave a viscous colourless oil that was triturated with dry ether to produce a white powder.

$^1$H NMR: $\delta$H (CDCl$_3$); 7.35–7.27 (5H, m), 5.09 (3H, br), 3.30 (2H, br q), 2.79 (4H, s), 2.66 (2H, t), 1.97 (2H, pentet).

Tris(trimethylsilyl)phosphite (900 mg, 3 mmol) was added to a solution of succinyl 4-[(benzyloxycarbonyl) amino]butanoate (340 mg, 1 mmol) in dioxane (0.5 ml) and the mixture warmed at 65–70° C. with the exclusion of moisture until shown by $^{31}$P NMR spectroscopy to be completed. Bromotrimethylsilane (0.5 g, 3.25 mmol) was added and the solution stirred for ca 1 h at room temperature. Volatile components were removed in vacuo to leave a viscous oil. Methanol (20 ml) was added and the resulting mixture stirred for 1 h. The solid product was then filtered off. More product precipitated on addition of acetone to the filtrate and this was added to the filtered solid. After drying the required bisphosphonate (compound 3) was obtained as a white solid (130 mg, 52%).

$\delta_P$ 19.5, $\delta_C$ (D$_2$O) 73.0 (t, J$_{PC}$=138 Hz), 39.9 (s), 27.0 (t, J$_{PC}$=7 Hz), $\delta_H$(D$_2$O) 2.76 (2H, m, CH$_2$N), 1.75 (4H, m, CH$_2$CH$_2$).

EXAMPLE 4

Solid Phase Synthesis of 4-Amino-1-hydroxybutane-1.1 bisphosphonic Acid (compound 3)

To 0.5 g of 2-chlorotrityl chloride resin suspended in anhydrous dimethylformamide was added 5 molar equivalents of β-alanine ethyl ester hydrochloride and 10 molar equivalents of triethylamine. The resin was agitated for 48 hours and then washed exhaustively with dichloromethane and dimethylformamide. The ester was cleaved by the addition of KOH in dioxan and agitation for 8 hours. The resin was washed thoroughly with methanol and dichloromethane after filtration. Addition of N-hydroxy succinimide (5 molar equiv.) and dicyclohexylcabodiimide (5 molar equiv.) in dichloromethane with stirring for 24 hours afforded the activated ester. After filtration the resin was washed with methanol and dichloromethane. To this resin in dichloromethane was added tris(trimethylsilyl) phosphite (5 molar equiv.) and agitated for 48 hours at room temperature. The resin was then washed with dichloromethane and methanol followed by treatment with 10% trifluoroacetic acid in dichloromethane to cleave the product.

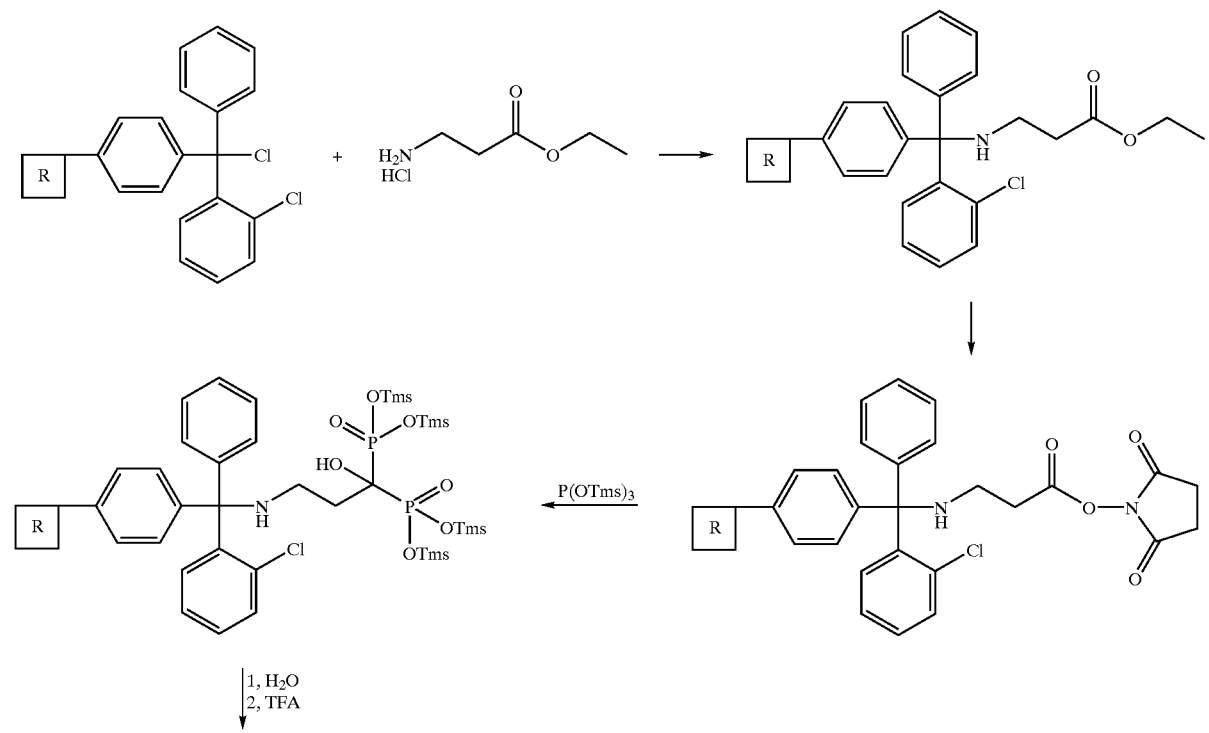

-continued

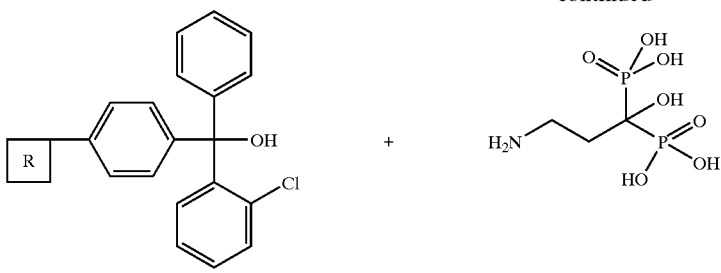

Synthetic route to an amino-bisphosphonate on a solid support

What is claimed is:

1. A method of preparation of a bisphosphonate, which method comprises reacting a tris(silyl)phosphite with an activated carbonyl compound and hydrolysing the resulting intermediate according to the reaction scheme:

$$P(OX)_3 + RCO.Y \rightarrow Intermediate \rightarrow RC(OH)(PO.[OH]_2)_2$$

where each X is the same or different and is tri-($C_1$–$C_{12}$ hydrocarbyl)silyl, R is $C_1$–$C_{12}$ primary, secondary or tertiary aminoalkyl, and Y is an active ester, N-hydroxysuccinimide or $PO(OR''')_2$, where R''' is $C_{1-12}$ alkyl or X.

2. The method of claim 1, wherein X of $P(OX)_3$ is trimethylsilyl.

3. The method of claim 1, wherein the tris(silyl)phosphite $P(OX)_3$ has artificially high proportion of $^{32}P$ or $^{33}P$.

4. The method of claim 1, performed at ambient temperature.

5. The method of claim 1, wherein Y is an active ester or N-hydroxysuccinimide and the Intermediate has the formula $RC(OZ)(PO.[OX]_2)_2$ where Z is H or X.

6. The method of claim 1, wherein Y is $PO(OR''')_2$ and the Intermediate has the formula $RC(OZ)(PO)[OX]_2)(PO[OR''']_2)$.

7. The method of claim 1, wherein the tris(silyl)phosphite $P(OX)_3$ or the activated carbonyl compound RCO.Y is immobilised on a solid support.

8. A radiolabelled phosphorus compound of the formula $$R'_q{}''P(OX)_{3-q}$$

wherein

R' is $C_1$–$C_{12}$ alkyl or aryl, q is 0, 1 or 2, n is at least partly 32 or 33 whereby the compound has an artificially high proportion of $^{32}P$ or $^{33}P$, X is tri-($C_1$–$C_{12}$ hydrocarbyl)silyl, and may be the same as or different from other X's.

9. The radiolabelled phosphorus compounds of claim 8, where q is 0 and X is trimethylsilyl.

10. A radiolabelled biphosphonate of the formula $$R''C(OH)(''PO[OH]_2)_2$$

wherein n is at least partly 32 or 33 whereby the compound has an artificially high proportion of $^{32}P$ or $^{33}P$, and R'' is $C_1$–$C_{12}$ primary, secondary or tertiary aminoalkyl or a derivative of these, or a substituted alkyl group having nitrogen as part of a hetreocyclic ring system.

11. The radiolabelled biphosphonate of claim 10, where R'' is —$(CH_2)_pNQ_2$, p is 2 or 3, and Q is H or $C_{1-5}$ alkyl.

12. A method of treating a patient suffering from osteosarcoma or bone metastases, which method comprises administering to the patient an effective amount of the radiolabelled biphosphonate of claim 11.

13. A compound of the formula $$RC(OZ)(PO[OX]_2)_2 \text{ or } RC(OZ)(PO[OX]_2)(PO[OR'''])$$

wherein

X is tri-($C_1$–$C_{12}$ hydrocarbyl)silyl, and may be the same as or different from other X's, Z is H or X, R''' is $C_1$–$C_{12}$ alkyl or X, and R is $C_1$–$C_{12}$ primary, secondary or tertiary aminoalkyl.

14. The compounds of claim 13, having an artificially high proportion of $^{32}P$ or $^{33}P$.

* * * * *